(12) United States Patent
Hogdahl et al.

(10) Patent No.: US 8,376,997 B2
(45) Date of Patent: Feb. 19, 2013

(54) DEVICE FOR DELIVERING MEDICAMENT

(75) Inventors: Stefan Hogdahl, Stockholm (SE);
Anders Karlsson, Saltsjobaden (SE)

(73) Assignee: SHL Group AB, Nacka Strand (SE)

( * ) Notice: Subject to any disclaimer, the term of this patent is extended or adjusted under 35 U.S.C. 154(b) by 238 days.

(21) Appl. No.: 12/679,583

(22) PCT Filed: Apr. 15, 2008

(86) PCT No.: PCT/EP2008/054548
§ 371 (c)(1),
(2), (4) Date: Jun. 3, 2010

(87) PCT Pub. No.: WO2008/155144
PCT Pub. Date: Dec. 24, 2008

(65) Prior Publication Data
US 2010/0298781 A1    Nov. 25, 2010

(30) Foreign Application Priority Data
Jun. 19, 2007 (SE) ...................................... 0701553

(51) Int. Cl.
*A61M 5/20* (2006.01)
(52) U.S. Cl. ................... 604/134; 604/207; 604/208
(58) Field of Classification Search .......... 604/207–208, 604/210–211, 218, 131, 134–138
See application file for complete search history.

(56) References Cited

U.S. PATENT DOCUMENTS

| | | | |
|---|---|---|---|
| 4,659,327 A | 4/1987 | Bennett et al. | |
| 6,599,272 B1 * | 7/2003 | Hjertman et al. | 604/209 |
| 2007/0197976 A1 | 8/2007 | Jacobs et al. | |
| 2008/0114305 A1 | 5/2008 | Gerondale | |

FOREIGN PATENT DOCUMENTS

| | | |
|---|---|---|
| WO | 00/69488 | 11/2000 |
| WO | 01/87384 | 11/2001 |
| WO | 2004/093949 | 11/2004 |
| WO | 2005/097233 | 10/2005 |
| WO | 2006/020756 | 2/2006 |

* cited by examiner

*Primary Examiner* — Theodore Stigell
(74) *Attorney, Agent, or Firm* — Edwards Wildman Palmer LLP; Steven M. Jensen

(57) ABSTRACT

The present invention relates to a device for expelling a predetermined quantity of medicament comprising driving means comprising an energy-accumulating member, a nut, and a driver for driving a pressure means; and activation means for activating said driving means wherein said pressure means comprises a movable wall part arranged inside a 2 container and a threaded plunger rod arranged to interact with said driving means for pushing said movable wall part forwardly, and wherein said activation means comprises a manually operated push button arranged on the front end of the device for promoting an ergonomic handling of the device and wherein said activation means are capable of interacting with said driving means in a stepwise mode; such that each time said push button is depressed said pressure means moves an step exerting pressure on the medicament inside the container and expelling a predetermined quantity of the medicament through the opening.

15 Claims, 5 Drawing Sheets

DEVICE FOR DELIVERING MEDICAMENT

TECHNICAL FIELD

Figure 1:
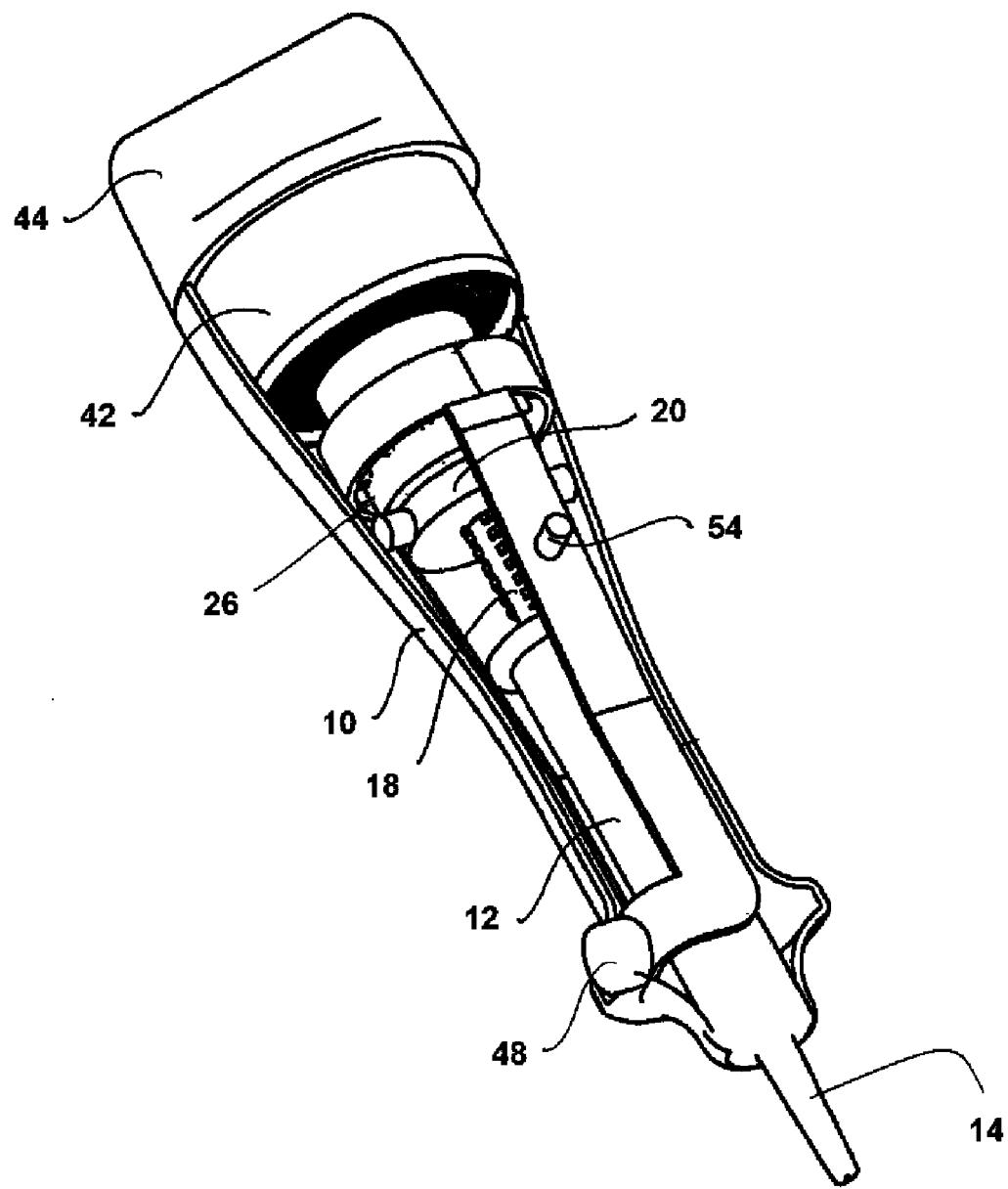

The present invention relates to a device for delivering medicament, and in particular in connection with medicament containing devices where the medicament is in a container and is exposed to pressure when the medicament is to be delivered in multiple predetermined quantities on multiple delivery sites in a stepwise mode.

BACKGROUND ART

Nowadays on the medical delivery device market, there are numerous devices for delivering medicament and also patented where the medicament is arranged in a container, such as a syringe, cartridge and the like, and wherein the medicament is exposed to pressure when it is to be delivered. The most common design is a generally tubular compartment having a stopper in one end of the compartment and a delivery opening e.g. a needle, attached to the opposite end of the compartment.

In order to deliver a quantity of medicament, the stopper is exposed to pressure, i.e. pushed into the compartment by a plunger rod, which could be done manually by a finger of a physician or trained person, which is the case for simple handheld hypodermic syringes.

In many instances it is desirable to be able to deliver multiple specified quantities of the medicament on multiple delivery sites in a stepwise mode. This is for example the case with manually operative mechanisms for moving a plunger rod as disclosed in the International Application Publication WO2006/020756 A2 and in the U.S. Pat. No. 4,512,767. The problem of said devices resides in the accuracy of the doses. If the actuation button is not fully depressed smaller doses cannot be delivered. Another example is the case with a multi-dose injection device, which is capable of delivering a number of specified, set doses until the compartment is empty, as disclosed in the European patent application No. 05104734.8 where specific doses can be set before injection. The injection device disclosed in said European patent application is arranged with spring means for exerting a pressure on the medicament for delivering a specific dose, i.e. pushing the plunger rod and thus the stopper into the container. The delivery of a dose requires a certain force from the spring means in order to overcome the friction between the somewhat resilient stopper and the inner surface of the container and also to be able to press the medicament in liquid form through a rather small passage in the needle, possibly within a predetermined time.

Typically, when a medicament/substance is to be delivered in multiple predetermined small quantities on multiple delivery sites in a stepwise mode, said medicament/substance quantities are injected manually, i.e. a normal type of syringe is used. In some treatments said medicament/substance has a high viscosity. Because of the rather large forces required for injecting said substances, and also due to the many small injections needed for a treatment, it is tiresome for the operator to use such a syringe during a treatment. The problem of the device disclosed in the European patent application resides in the degree of ergonomics when the medicament is to be delivered in multiple predetermined quantities on multiple delivery sites in a stepwise mode.

Moreover, a further example is the case with a multiple, metered dosage dispensing device as disclosed in the U.S. Pat. No. 4,659,327; wherein the device comprises an elongated body with an ampule containing material to be dispensed, a piston movable against the material to discharge from a nozzle, a ribbed plunger rod linearly movable by a pressure device against the piston to discharge material and an stop and release toothed unit movable intermediately of the ends of the body between a depressed and an undepressed position respectively to engage a pair of racks of teeth on the ribbed plunger rod. When said stop and release toothed unit is depressed, said unit allows the plunger and the piston to move linearly a predetermined increment, to stop said movement and to maintain the plunger in a stopped position until the unit is depressed again. The problem of the device disclosed in the U.S. Pat. No. 4,659,327, resides especially in the possibility of delivering accurately very small doses, as in the range of 0.01 ml.-0.005 ml., since the plunger rod, which is not adapted to be rotatable, and the stop and release toothed unit are designed having a gearing which is not adapted for such small doses.

There are thus a number of aspects that are addressed with the present invention.

DISCLOSURE OF INVENTION

The aim of the present invention is to remedy a number of drawbacks and problems associated with the state of the art devices of the above mentioned type and to provide improvements that facilitate the handling and accuracy of medical delivery devices, and especially when delivering multiple small predetermined quantities on multiple delivery sites in a stepwise mode.

This aim is achieved with a device according to claim 1. Preferable embodiments of the present invention are subject of the dependent claims.

According to a main aspect of the present invention is characterized by a device for delivering medicament comprising a container arranged to contain medicament, which container further comprises an opening arranged to expel medicament from the container; pressure means arranged to exert pressure on the medicament inside the container for expelling a predetermined quantity of the medicament through the opening; driving means comprising an energy accumulating member, a nut, and a driver for driving said pressure means; and activation means for activating said driving means wherein said pressure means comprises a movable wall part arranged inside the container and a threaded plunger rod arranged to interact with said driving means for pushing said movable wall part forwardly, and wherein said activation means comprises a manually operated push button arranged on the front end of the device for promoting an ergonomic handling of the device and wherein said activation means are capable of interacting with said driving means in a stepwise mode; such that each time said push button is depressed said pressure means moves an step exerting pressure on the medicament inside the container and expelling a predetermined quantity of the medicament through the opening.

According to another aspect of the invention, said device comprises a tensioning knob arranged and designed to interact with said energy accumulating member such that when said tensioning knob is actuated, said energy accumulating member is tensioned.

Yet, according to another aspect of the invention, said energy accumulating member is arranged and designed to be in a pre-tensed state.

Further, said device is suitable for the use within the area of injecting cosmetic substances.

The advantages with the present invention are several. Accurate small doses each time the press button is actuated. Ergonomic handling of the device when a medicament/substance is to be delivered in multiple predetermined small quantities on multiple delivery sites in a stepwise mode, due to the position of the push button on the front end of the device. These and other aspects of and advantages with the present invention will become apparent from the following detailed description of the invention and from the accompanying drawings.

BRIEF DESCRIPTION OF FIGURES IN THE DRAWINGS

Figure 2:
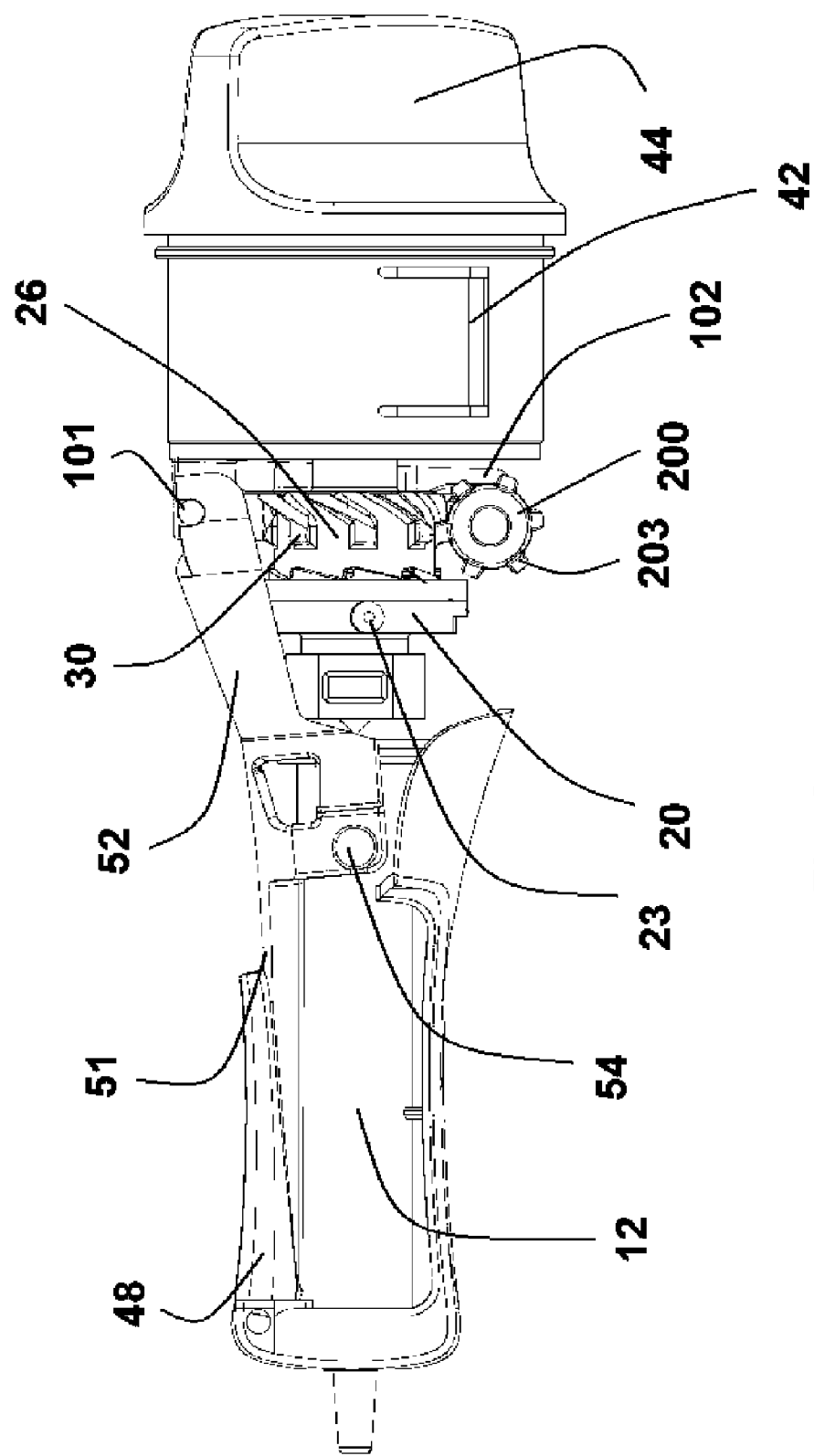
Figure 3:
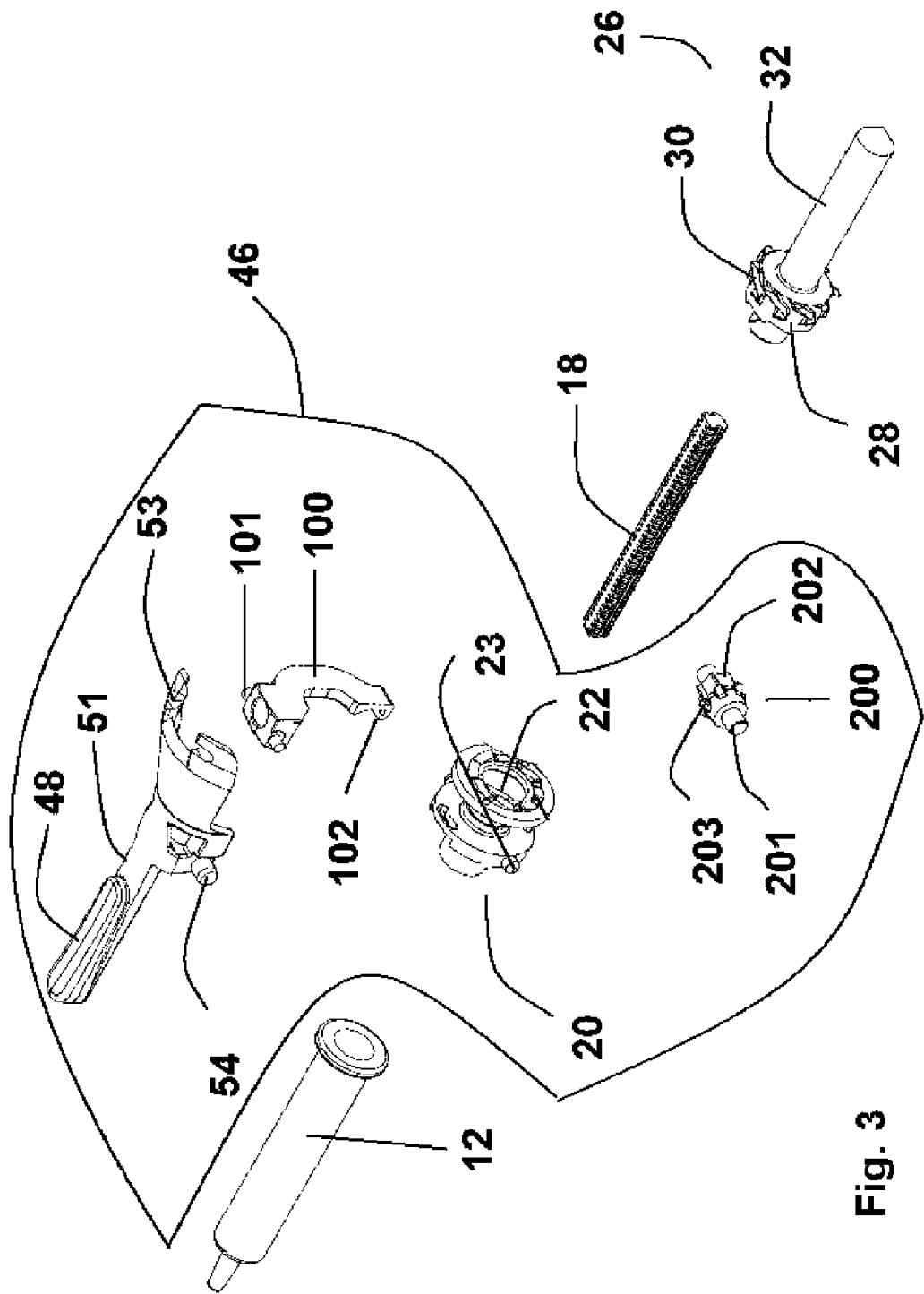
Figure 4:
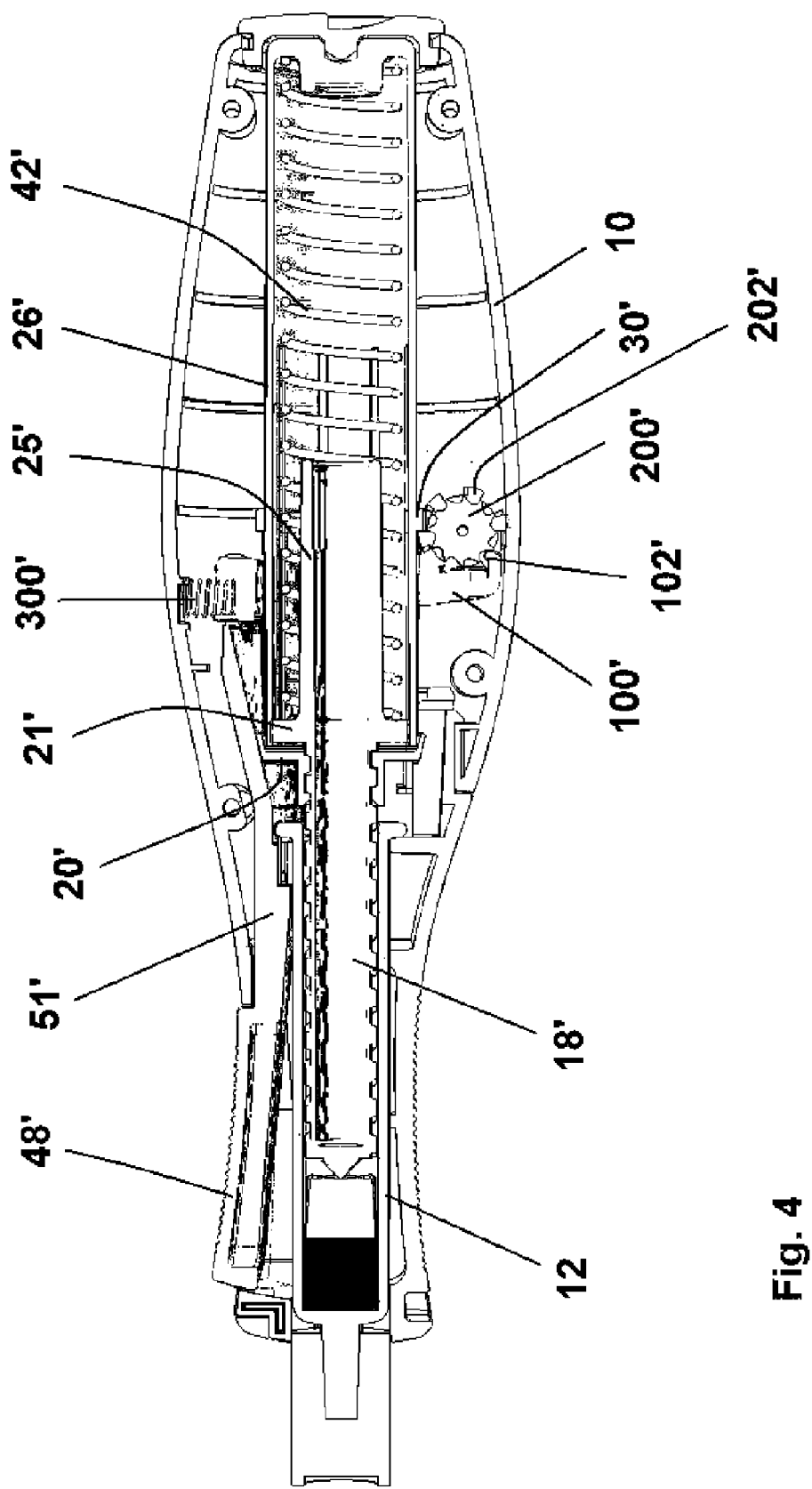
Figure 5:
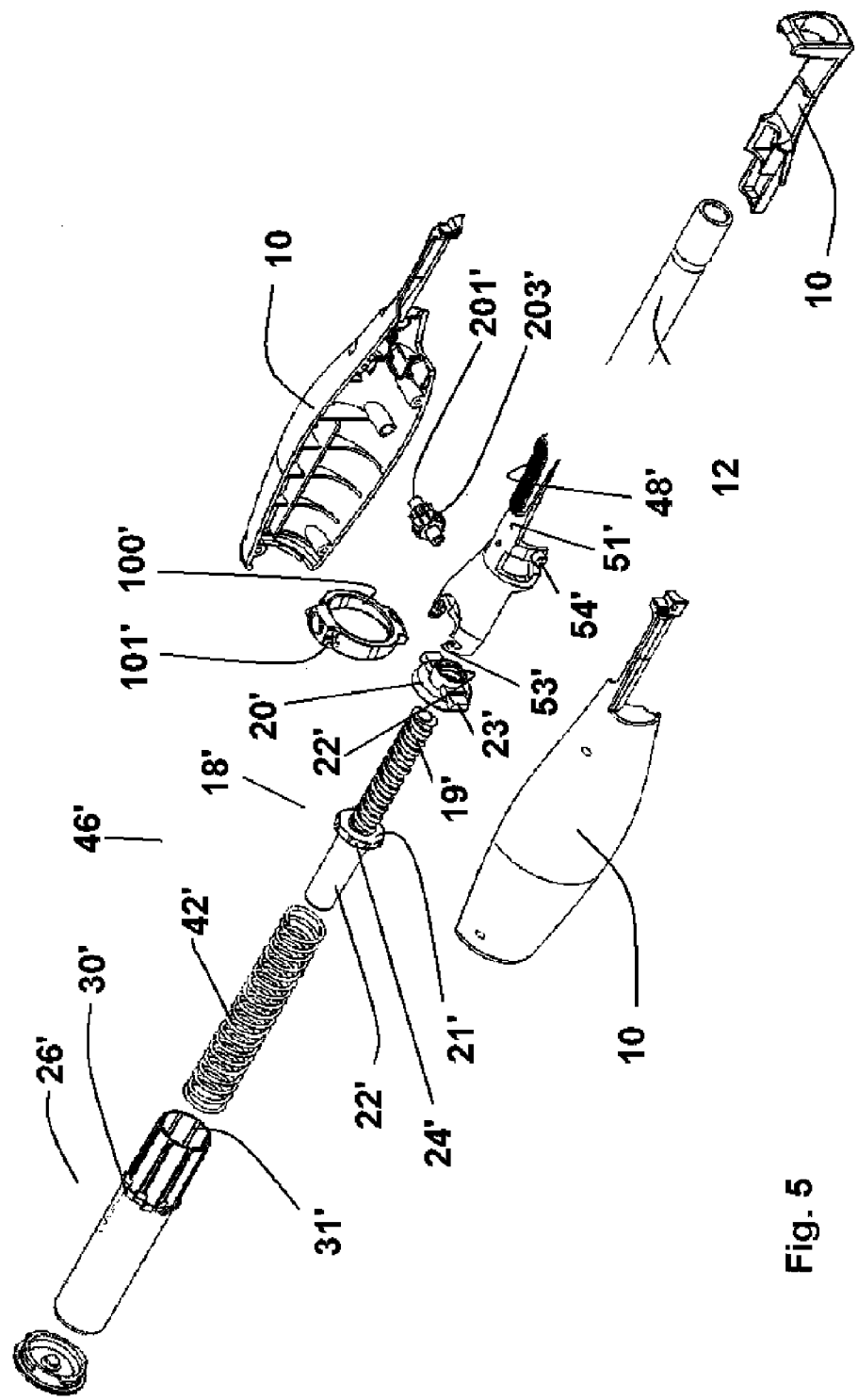

In the following detailed description of the invention, reference will be made to the accompanying drawings, of which FIG. 1 shows an injection device according to the present invention, FIG. 2 shows a first embodiment of an injection device according to the present invention, FIG. 3 shows an exploded view of activation means of the injection device according to FIG. 2, FIG. 4 shows a second embodiment of an injection device according to the present invention, FIG. 5 shows an exploded view of the injection device according to FIG. 4.

DETAILED DESCRIPTION OF THE INVENTION

FIG. 1 shows a non-limiting example of a medicament delivery device of the present invention. The delivery device comprises a housing 10 designed to be held in one hand for delivering repeated small quantities of medicament step by step. Inside and at the front end of the housing a medicament containing container 12 is arranged having a front end onto which an opening 14 e.g. a needle, may be attached. Said medicament delivery device comprises pressure means including a movable wall part, hereafter called stopper, arranged inside the container; and a pressure member 18 as a plunger rod, arranged to push on the stopper forwardly. The front end of the plunger rod is preferably pointed against a spinner to minimize the friction between the plunger rod and the stopper. Said medicament delivery device also comprises driving means including an energy accumulating member 42, a nut 20 and a driver 26.

The Delivery Device of the Present Invention According to a First Embodiment

FIGS. 2, 3 refer to a first configuration of the delivery device wherein the energy accumulating member 42 has to be tensioned before medicament delivery. Further, the nut 20 is adapted to be in a non-rotating state due to two outwardly protruding pivoting pins 23 journalled in the housing, wherein said nut 20 has a through-going central bore 22 having corresponding threads as the plunger rod. The driver 26, FIG. 3, is hollow and further arranged around the plunger rod in a rotationally locked position. The driver has a lower, first cylindrical front portion 28 having a number of outwardly directed protrusions 30 evenly spaced around its circumference where the distance between two adjacent protrusions constitutes a certain predetermined dose quantity, and a second elongated cylindrical portion 32.

Further the energy accumulating member 42, e.g. a flat spring, is wound around the second portion of the driver having its inner end attached to the driver 26. A tensioning knob 44 is arranged at the rear end of the delivery device, to which the outer end of the spring 42 is attached.

An activation mechanism 46, as seen in FIG. 3, is also arranged on the delivery device. It comprises a push button 48 protruding through a slot on the front end of the housing for promoting an ergonomic handling of the device. The push button is attached to an arm 51 on a side of the container and plunger rod. Two outwardly protruding pivoting pins 54 are arranged on the arm, which pivoting pins are journalled in the housing. The rear end of the arm comprises a wing formed part 52 having slots 53. An intermediate lever 100 partially arranged around the cylindrical portion 32 of the driver 26 comprises two outwardly protruding pivoting pins 101 positioned on the slots 53, and a ledge 102 arranged to be in contact with one of the teeth 202 on a pinion 200; wherein said pinion also comprises pins 201 that are journalled in the housing, and teeth 203 evenly spaced around its circumference.

When the delivery device is adapted to be used, a needle is attached to the container by suitable means and a needle sheath is removed. The tensioning knob 44 is then actuated whereby the energy accumulating member 42 is tensioned. The driver is prevented from turning due to that one of the teeth 203 of the pinion 200 is in contact with one of the protrusions 30 of the driver, thereby holding the driver against rotation.

When an injection is to be performed, the needle is penetrated on a suitable location on the skin, and the push button 48 is pressed. The pressing of the push button causes the activation mechanism to pivot around the pivoting pins 54. This in turn causes the ledge 102 of the intermediate lever 100 to move the pinion 200 whereby one of the tooth 203 of the pinion 200 that is in contact with one of the protrusions 30 comes out of contact and the driver rotates a certain increment distance until a further tooth 203 of the pinion 200 come into contact with a further protrusion 30 and thereby locking the drive wheel from rotation.

The rotation of the driver 26 causes the plunger rod 18 to rotate. Due to the force from the energy accumulating member 42 and the threaded engagement between the plunger rod and the nut 20, the plunger rod moves forwardly pushing on the stopper whereby the medicament is expelled through the needle.

In this it is to be understood that the distance between the protrusions 30 of the driver, together with the pitch of the thread of the plunger rod constitutes a certain predetermined dose quantity. I.e. in order to set a specific dose, which is done during manufacture of the device, a certain distance is chosen between the protrusions as well as a certain pitch of the threads of the plunger rod. This gearing mechanism is adapted for delivering small doses, especially in the range of 0.01 ml.-0.005 ml.

Said first configuration is more suitable for medicaments or substances having high viscosity.

The Delivery Device of the Present Invention According to a Second Embodiment

FIGS. 4, 5 refer to a second configuration of the delivery device wherein the manufacturer of the device delivers the device with the energy accumulating member 42' in a pretensed state. The driver 26' of said second configuration is tube-shaped having a number of dose step protrusions 30' equally distributed along its outer circumference and having longitudinally grooves 31' equally distributed along its inner circumference. Moreover, the plunger rod 18' of said second configuration has a threaded part 19' and a non-threaded part 25', wherein said parts are divided by a disc 21'. Further, said disc has protrusions 24' along its circumference accommodated on said longitudinally grooves 31' of said driver, such that the plunger rod extends through the driver in a rotationally locked, but in a slidable mode. The nut 20' is adapted to be in a non-rotating state due to two outwardly protruding pivoting pins 23' journalled in the housing. Said nut 20' has also a through-going central bore 22' having corresponding threads as the threaded part 19' of the plunger rod. The energy accumulating member 42' is arranged inside said driver 26' between an inner surface of the distal end of said driver 26' and the rear end of the disc 21'.

An activation mechanism 46', as seen in FIG. 5, is also arranged on the delivery device, wherein said activation mechanism 46' comprises a push button 48' protruding through a slot on the front end of the housing for promoting an ergonomic handling of the device. The push button is attached to an arm 51' on a side of the container and plunger rod. Two outwardly protruding pivoting pins 54' are arranged on the arm, which pivoting pins are journalled in the housing. The rear end of the arm, comprises a wing formed part 52' having slots 53'. An intermediate lever 100' having a larger diameter than the outer diameter of the driver 26', is arranged around the outer surface of said driver 26'. Further, said intermediate lever 100' comprises two outwardly protruding pivoting pins 101' positioned on the slots 53', and a ledge 102' arranged to be in contact with one of the teeth 202' on a pinion 200'; wherein said pinion also comprises pins 201' that are journalled in the housing, and teeth 203' evenly spaced around its circumference. A resilient means 300' e.g. a coil spring is arranged between a slot on the housing and a slot on the lever 100', as seen in FIG. 4.

When the delivery device is adapted to be used, a needle is attached to the container by suitable means and a needle sheath is removed. The driver is prevented from turning due to that one of the teeth 203' of the pinion 200' is in contact with one of the protrusions 30' of the driver, thereby holding the driver against rotation.

When an injection is to be performed, the needle is penetrated on a suitable location on the skin, and the push button 48' is pressed. The pressing of the push button causes the activation mechanism to pivot around the pivoting pins 54'. This in turn causes the ledge 102' of the intermediate lever 100' to move the pinion 200' whereby one of the teeth 203' of the pinion 200' that is in contact with one of the protrusions 30' comes out of contact and the driver rotates a certain increment distance until a further tooth 203' of the pinion 200' come into contact with a further protrusion 30' and thereby locking the drive wheel from rotation.

The rotation of the driver 26' causes the plunger rod 18' to rotate. Due to force from the energy accumulating member 42' and the threaded engagement between the threaded part 19' of the plunger rod and the nut 20', the plunger rod moves forwardly pushing the stopper whereby the medicament is expelled through the needle.

In this it is to be understood that the distance between the protrusions 30' of the driver, together with the pitch of the thread of threaded part 19' of the plunger rod constitutes a certain predetermined dose quantity. I.e. in order to set a specific dose, which is done during manufacture of the device, a certain distance is chosen between the protrusions as well as a certain pitch of the threads of the plunger rod.

Said second configuration is more suitable for medicaments or substances having low viscosity.

Moreover, in the currently preferred designs, the dose increment steps are in the order of 0.01 ml-0.005 ml per step and one dose increment step of 0.01 ml corresponds to a clock-wise rotation of the drive wheel with 45°.

It is to be understood that the embodiments described above and shown on the drawings are to be regarded only as non-limiting examples of the invention and that it can be modified in many ways within the scope of the patent claims.

The invention claimed is:

1. Device for delivering medicament, comprising:
a container arranged to contain medicament, which container further comprises an opening arranged to expel medicament from the container;
pressure means arranged to exert pressure on the medicament inside the container for expelling a predetermined quantity of the medicament through the opening;
driving means comprising an energy accumulating member, a nut and a driver for driving said pressure means; and
activation means for activating said driving means,
wherein said pressure means comprises a movable wall part arranged inside the container and a threaded plunger rod arranged to interact with said driving means for pushing said movable wall part forwardly due to force from the energy accumulating member and a threaded engagement between the plunger rod and the nut,
said activation means comprises a manually operated push button arranged on the front end of the device for promoting an ergonomic handling of the device, and
said activation means is capable of interacting with said driving means in a stepwise mode, such that each time said push button is depressed, said pressure means moves a step exerting pressure on the medicament inside the container and expelling a predetermined quantity of the medicament through the opening.

2. Device according to claim 1, wherein said device comprises a tensioning knob arranged and designed to interact with said energy accumulating member such that when said tensioning knob is actuated, said energy accumulating member is tensioned.

3. Device according to claim 1, wherein said energy accumulating member is arranged and designed to be in a pretensed state.

4. Device according to claim 1, wherein said nut is arranged and designed to be in a non-rotating state due to two outwardly protruding pivoting pins journalled in the housing, and wherein said nut has a through-going central bore having corresponding threads as the plunger rod.

5. Device according to claim 1, wherein said driver comprises a number of outwardly directed protrusions evenly spaced around its circumference, and wherein the distance between two adjacent protrusions constitutes a certain predetermined dose quantity.

6. Device according to claim 1, wherein said activation means comprises an arm on which said push button is arranged, a pinion and an intermediate lever, wherein upon the activation of said push button said arm is capable of interacting with said intermediate lever and said pinion correspondingly, and wherein said pinion is arranged and designed to interact with said driver and said pressure means for expelling a predetermined quantity of the medicament through the opening.

7. Device according to claim 6, wherein said pinion has protrusions arranged and designed to interact with protrusions of the driver which is arranged around the plunger rod in a rotationally locked position.

8. Device according to claim 1, wherein the medicament comprises cosmetic substances.

9. Device for delivering medicament, comprising:
a container arranged to contain medicament, which container further comprises an opening arranged to expel medicament from the container;
pressure means arranged to exert pressure on the medicament inside the container for expelling a predetermined quantity of the medicament through the opening;
driving means comprising an energy accumulating member, a nut and a driver for driving said pressure means; and
activation means for activating said driving means,
wherein said pressure means comprises a movable wall part arranged inside the container and a threaded plunger rod arranged to interact with said driving means for pushing said movable wall part forwardly,
said activation means comprises a manually operated push button arranged on the front end of the device for promoting an ergonomic handling of the device,
said activation means is capable of interacting with said driving means in a stepwise mode, such that each time said push button is depressed, said pressure means moves a step exerting pressure on the medicament inside the container and expelling a predetermined quantity of the medicament through the opening, and
said nut is arranged and designed to be in a non-rotating state due to two outwardly protruding pivoting pins journalled in the housing, and wherein said nut has a through-going central bore having corresponding threads as the plunger rod.

10. Device according to claim 9, wherein said device comprises a tensioning knob arranged and designed to interact with said energy accumulating member such that when said tensioning knob is actuated, said energy accumulating member is tensioned.

11. Device according to claim 9, wherein said energy accumulating member is arranged and designed to be in a pretensed state.

12. Device according to claim 9, wherein said driver comprises a number of outwardly directed protrusions evenly spaced around its circumference, and wherein the distance between two adjacent protrusions constitutes a certain predetermined dose quantity.

13. Device according to claim 9, wherein said activation means comprises an arm on which said push button is arranged, a pinion and an intermediate lever, wherein upon the activation of said push button said arm is capable of interacting with said intermediate lever and said pinion correspondingly, and wherein said pinion is arranged and designed to interact with said driver and said pressure means for expelling a predetermined quantity of the medicament through the opening.

14. Device according to claim 13, wherein said pinion has protrusions arranged and designed to interact with protrusions of the driver which is arranged around the plunger rod in a rotationally locked position.

15. Device according to claim 9, wherein the medicament comprises cosmetic substances.

* * * * *